United States Patent [19]
Struble

[11] Patent Number: 6,148,234
[45] Date of Patent: Nov. 14, 2000

[54] DUAL SITE PACING SYSTEM WITH AUTOMATIC PULSE OUTPUT ADJUSTMENT

[75] Inventor: Chester Struble, Eijsden, Netherlands

[73] Assignee: Medtronic Inc., Minneapolis, Minn.

[21] Appl. No.: 09/161,237

[22] Filed: Sep. 28, 1998

[51] Int. Cl.$^7$ .................................................. A61N 1/368
[52] U.S. Cl. ............................................. 607/28; 607/11
[58] Field of Search .................. 607/27, 28, 11, 607/123

[56] References Cited

U.S. PATENT DOCUMENTS

| | | | |
|---|---|---|---|
| 5,165,404 | 11/1992 | Andersson et al. | 128/419 PG |
| 5,165,405 | 11/1992 | Eckwall | 128/419 PG |
| 5,172,690 | 12/1992 | Nappholz et al. | 128/419 PG |
| 5,222,493 | 6/1993 | Sholder | 128/419 PG |
| 5,285,780 | 2/1994 | Tsuji et al. | 607/13 |
| 5,320,643 | 6/1994 | Roline et al. | 607/28 |
| 5,324,310 | 6/1994 | Greeninger et al. | 607/28 |
| 5,601,615 | 2/1997 | Markowitz et al. | 607/28 |
| 5,713,933 | 2/1998 | Baxter et al. | 607/28 |
| 5,800,465 | 9/1998 | Thompson et al. | 607/123 |
| 5,861,008 | 1/1999 | Obez et al. | |
| 5,902,325 | 5/1999 | Condie et al. | |

*Primary Examiner*—Carl H. Layno
*Attorney, Agent, or Firm*—Thomas F. Woods; Michael J. Jaro; Howard Patton

[57] ABSTRACT

There is provided a dual site pacing system, either bi-ventricular or bi-atrial, wherein the pacemaker looks for a signal sense during the refractory period following delivery of the pulse pair. If the threshold of either heart chamber has risen above the level of the delivered pulses, that chamber will not be captured, and will not have an inherent refractory period following delivery of the pulse pair. Under these circumstances, and where the patient has conduction delay from one chamber to the other, e.g., LBBB or RBBB, the excitation signal from the other chamber will be sensed in the non-captured chamber during the pacemaker refractory period. Such a sensing during the pacemaker refractory period is recognized to result from loss of capture, and is utilized to automatically increase pulse output back up to a safe level above threshold.

13 Claims, 4 Drawing Sheets

DUAL SITE PACING SYSTEM WITH AUTOMATIC PULSE OUTPUT ADJUSTMENT

FIELD OF THE INVENTION

This invention lies in the field of bi-ventricular and other dual site cardiac pacing systems and, more particularly, dual site pacing systems which monitor for loss of capture at either site and respond to detection of loss by increasing the output level of the delivered pacing pulses to a safe level above threshold.

BACKGROUND OF THE INVENTION

The benefits of four chamber pacing have become widely apparent in recent years, and have generally been disclosed and published in the literature. Cazeau et al., PACE, vol.17, November 1994, Part II, pp. 1974–1979, disclose investigations leading to the conclusion that four-chamber pacing is feasible; and that in patients with evidence of interventricular dyssynchrony a better mechanical activation process can be obtained by resynchronizing the polarization of the right and left ventricles, and optimizing the AV sequence on both sides of the heart. In the patent literature, U.S. Pat. No. 4,928,688 is representative of a system for simultaneous left ventricular (LV) and right ventricular (RV) pacing, known as "bi-ventricular" pacing. In this system, natural ventricular depolarizations are sensed in both chambers, and if one chamber contracts but the other one does not within a short time interval, then the non-contracting chamber is paced.

Bi-ventricular pacing, or more generally four-chamber pacing, is a response to the ongoing quest to provide better pacing therapy for patients with congestive heart failure (CHF). CHF is defined generally as the inability of the heart to deliver enough blood to the peripheral tissues to meet metabolic demands. Frequently CHF is manifested by left heart dysfunction, but it can have a variety of sources. For example, CHF patients may have any one of several different conduction defects. The natural electrical activation system through the heart involves sequential events starting with the sino-atrial (SA) node, and continuing through the atrial conduction pathways of Bachmann's bundle and internodal tracts at the atrial level, followed by the atrio-ventricular (AV) node, Common Bundle of His, right and left bundle branches, and final distribution to the distal myocardial terminals via the Purkinje fiber network. A common type of intra-atrial conduction defect is known as intra-atrial block (IAB), a condition where the atrial activation is delayed in getting from the right atrium to the left atrium. In left bundle branch block (LBBB) and right bundle branch block (RBBB), the activation signals are not conducted in a normal fashion along the right or left bundle branches respectively. Thus, in a patient with bundle branch block, the activation of the ventricle is slowed, and the QRS is seen to widen due to the increased time for the activation to traverse the conduction path. For example, in a patient with LBBB, the delay in the excitation from the RV to the LV can be as high as 120 to 150 ms.

As used herein, the term bi-ventricular pacing refers to simultaneous or substantially simultaneous pacing of the two ventricles. Thus, pulses of exactly the same timing may be delivered to each ventricle, or, e.g., the pulse to the left ventricle may be delivered one or two ms before the pulse to the right ventricle. Likewise, it is known that there is an advantage to simultaneous or nearly simultaneous pacing of the left atrium and the right atrium for patients with IAB. In a patient with IAB, the left atrium may be excited to contract up to 90 ms later than the right atrium. It can be seen that if contractions in the left ventricle and the right ventricle are triggered at about the same time, then the left AV synchrony is impaired, with the left ventricle not having adequate time to fill up. The advantage of pacing the two atria for patients with IAB is disclosed at AHA, 1991, Abstract from 64th Scientific Sessions, "Simultaneous Dual Atrium Pacing in High Degree Inter-Atrial Blocks: Hemodynamic Results," Daubert et al., No. 1804. Thus, a pacing system may provide dual site pacing of the two ventricles, or the two atria, or both. Consequently, as used herein, the term "dual site" refers to pacing substantially simultaneously, or concurrently in either the ventricles or the atria.

It is recognized, of course, that dual site pacing will, as a general proposition, require roughly twice as much pulse power delivery to the patient's heart as corresponding single chamber pacing. In view of this, it becomes doubly important to ensure that the pacemaker reliably causes the myocardium of the heart chamber to contract or "beat," i.e., to "capture" the heart. Stimulation pulses, or pacing pulses provided by an implanted pacemaker, have well defined amplitude and pulse width characteristics which can be adjusted by remote programming and telemetry equipment, or automatically by the pacemaker, to meet physiologic and device power conservation needs of the particular patient in which the pacemaker is implanted. As used herein, the term "pulse output," or PO, refers to the energy of the delivered pacing pulse, which can be varied by adjusting the amplitude or the pulse width, or both.

The amplitude (strength) and pulse width (duration) of the pacing pulses must be of such an energy magnitude above the stimulation threshold that capture is maintained, in order to prevent serious complications and even death. Moreover, it is desirable that this energy is not higher than a reasonable "safety margin" above the stimulation threshold, in order to prolong battery life. The patient's stimulation thresholds in the different chambers often fluctuate in the short term, and gradually change in the long term. For dual site pacing, where the positioning of the pacing electrodes is quite different, e.g., comparing the left ventricle to the right ventricle, these thresholds will not be exactly the same. While the safety margin for each heart chamber to be paced is typically set by the physician at the time of implantation of the pacemaker system to account for projected chronic thresholds, there remains a need for chronically testing threshold, so as to track any changes in threshold and continually adjust PO to a proper level.

In prior art single chamber and dual chamber pacing systems, a great deal of effort has been expended to develop pacemakers having the capability of automatically testing the stimulation threshold, i.e., providing an "auto-capture" detection function, and resetting the pacing pulse energy to exceed the threshold by the safety margin without the need for clinical or patient intervention. A wide variety of approaches have been taken in the pacemaker art as reflected by the patent literature. See, for example, U.S. Pat. Nos. 5,324,310; 5,320,643; 5,165,404; 5,165,405; 5,172,690; 5,222,493; and 5,285,780. The capture detection threshold tracking approaches in the prior art have taken a variety of forms, and typically attempt to overcome the difficulty in detecting the evoked cardiac response wave shape from the pacing electrodes employed to deliver the pacing pulse. High stimulation energy pacing pulses and the ensuing after potentials and electrode-tissue polarization artifacts mask the evoked response, and also saturate the sense amplifiers coupled to the electrodes, until they dissipate. By the time that the sense amplifier is no longer "blinded," the evoked response, if any, has typically passed the electrodes. As a consequence, most of the prior art approaches rely on additional components and circuitry, and more complex logic, which consume energy, add to the bulk and cost of the system, and also raise reliability issues. This situation is, of course, worsened in the case of dual site pacing systems. There is thus an aggravated need in the area of dual site pacemakers to provide a reliable technique for determining whenever there is loss of capture (LOC) in either chamber, without compounding the circuitry and logic complexity of the pacemaker.

SUMMARY OF THE INVENTION

It is an object of the invention to provide an efficient and reliable means of determining occurrences of loss of capture in a dual site pacing system, e.g., for a biventricular pacing system, which can determine any occurrence of loss of capture in either the left or right ventricle; and to adjust pulse output accordingly to a safe level above threshold. The determination should preferably be made using circuitry and logic capability already in place, to optimize cost and reduce power consumption, while ensuring reliable detection.

The above object is accomplished in this invention by determining when an excitation signal is sensed during the refractory interval which follows delivery of the dual pulses. For a bi-ventricular pacing system, where pacing pulses are delivered substantially concurrently to both ventricles, when capture is achieved in both ventricles, no intrinsic depolarization signals can be sensed during the following refractory period. However, where the output level of one of the pacing pulses is insufficient to capture the ventricle, but capture is achieved in the other ventricle, a delayed depolarization pattern results in a "sense" in the ventricle where there was loss of capture. For example, for a heart with LBBB, failure to capture in the left ventricle results in a delayed depolarization in the left ventricle on the order of up to 120–150 ms. This delayed depolarization transferred from the right ventricle comes after the blanking period but during the left ventricular refractory period. Sensing of such a delayed signal during the refractory period (here referred to as a VR) is thus an indication of loss of capture (LOC).

In accordance with the above, there is provided a dual site pacing system with the capability of automatically detecting when there is LOC at one of the sites, either ventricular or atrial. Following each delivered pair of pacing pulses to the dual sites, the pacemaker times out an appropriate blanking interval, and then times out a refractory period to coincide with the heart chamber's normal period of refractoriness following a contraction. During the refractory interval, or refractory period (RP), the pacemaker looks to see if an excitation signal is sensed. If yes, this means that a chamber was not captured, and the excitation from the other chamber (which was captured by a delivered pulse) had been conducted to the non-captured chamber. Accordingly, a sense during the RP, herein called a VR, is used to logically indicate LOC. The pacemaker responds by automatically increasing PO of the delivered pulses. The pacemaker may have one sense channel for the two dual site chambers, and increase PO for both pulses upon detection of a VR; or may have dual channels, and increase PO only for the chamber from which the VR was detected.

DESCRIPTION OF THE PREFERRED EMBODIMENTS

Figure 1:
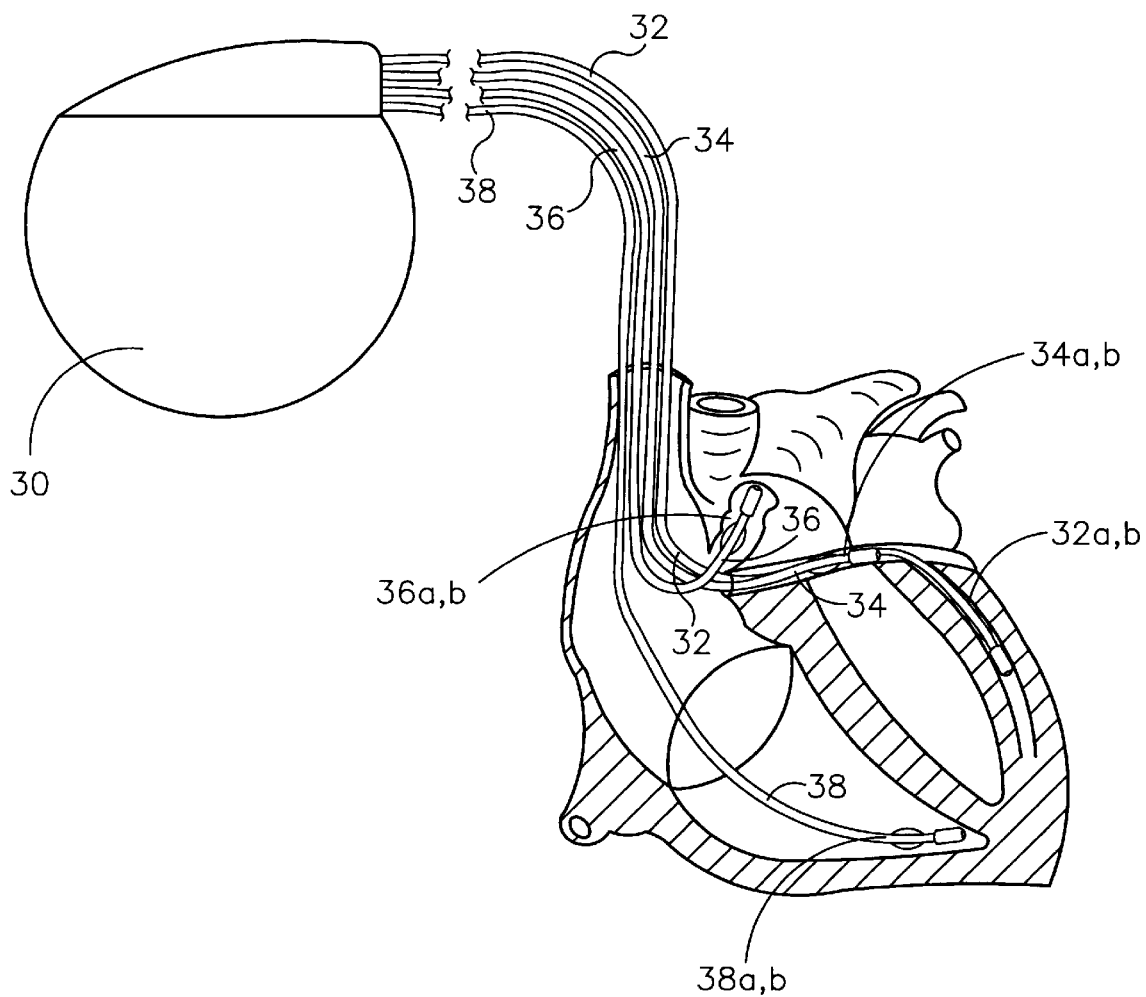
FIG. 1 is a schematic representation of a pacing system in accordance with this invention, showing dual atrial and dual ventricular pacing through four leads carrying electrodes positioned in each of the respective cardiac chambers.

Referring now to FIG. 1, there is shown a schematic representation of a four-chamber pacing system, illustrating four pacing leads providing bipolar electrodes positioned for pacing and sensing in each of the respective heart chambers, and also for impedance measurements. Pacing lead 38 is positioned conventionally such that its distal end is in the right ventricular apex position. It carries bipolar electrodes 38a and 38b adapted for pacing and sensing. Likewise, atrial lead 36 is positioned so that its distal end is positioned within the right atrium, with bipolar electrodes 36a, 36b. Lead 34 is passed through the right atrium, so that its distal end is positioned in the coronary sinus for pacing and sensing through electrodes 34a, b, as shown. Likewise, lead 32 is positioned via the coronary sinus to a cardiac vein, e.g., the middle or great cardiac vein, so that distal electrodes 32a and 32b are positioned approximately as shown for pacing and sensing with respect to the left ventricle. The pacing leads are connected to pacemaker 30 in a conventional manner. It is to be understood that each of the four leads can be a unipolar lead; different configurations are within the scope of the invention.

Figure 2:
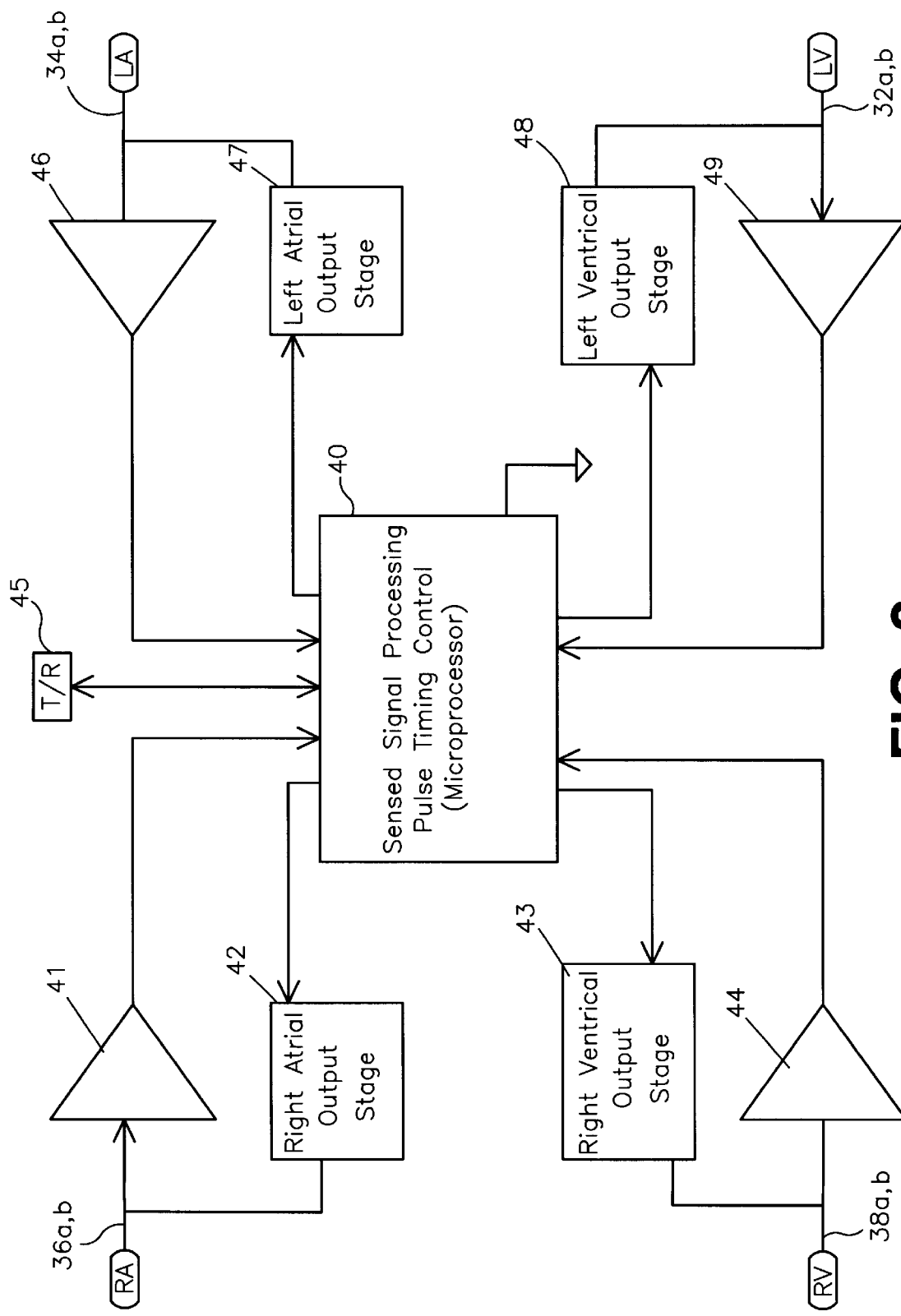
FIG. 2 is a block diagram of a pacing system in accordance with this invention, showing the primary pacemaker components for generating pace pulses and for receiving sensed signals.

Referring now to FIG. 2, there is shown a block diagram of the primary components of a pacing system in accordance with this invention. A control block 40 is illustrated, which typically contains a microprocessor as well as other circuitry, either IC or analog circuitry, for controlling pulse timing, processing sensed signals, and carrying out other well known pacemaker functions. Block 40 suitably contains memory to store data and functional software, and can receive reprogramming data through transmit/receive (T/R) block 45, which is downloaded from an external programmer. Block 40 may contain any desired combination of software and hardware, including DSP technology for processing sensed signals.

FIG. 2 illustrates transmitting output pulses and receiving signals from all four heart chambers. Thus, block 40 provides control signals to right atrial output stage 42, which generates pacing pulses transmitted to electrode(s) 36a, b; and signals sensed in the right atrium are amplified at 41 and transmitted back to control block 40 for processing and analysis. In a like manner, output stage 43 provides output pulses to the right ventricle, and amplifier 44 provides sense signals from the right ventricle; output stage 47 provides output pulses to the left atrium and amplifier 46 provides sense signals from the left atrium back to block 40; and output stage 48 provides pacing pulses to the left ventricle and amplifier 49 provides signals sensed from the left ventricle back to block 40. It is to be understood that while a four-chamber pacemaker as illustrated, the invention is applicable to any dual site pacing, i.e, bi-ventricular, bi-atrial, or both. Further, as stated above, for dual site pacing in either the ventricles or the atria, the two pulses of the pulse pair may be delivered simultaneously, or may be delivered with a slight time delay; and may be delivered serially or in parallel. In one embodiment, the pulse generator means may provide a single ventricular output stage which is connected to a lead which forks into left and right branches, thereby providing the same pulse to both ventricular electrode locations. In such an embodiment, there likewise would be just one sense amplifier path for delivering sense signals from either ventricle back to block 40.

The LOC detection feature of this invention is based on delivery of a pacing pulse, e.g., a VP, and a detection of a delayed depolarization due to Intraventricular Conduction Delay (IVCD). A delay from the RV to LV is LBBB; a delay from LV to RV is RBBB. The Ventricular Refractory Period (VRP) is typically set at about 230 ms, and a typical (IVCD) conduction delay within this period will be sensed as a VR. However, if the intrinsic conduction delay is extremely long (extreme IVCD), such that the delayed depolarization is greater than 230 ms, then the VRP will be reprogrammed to a longer value as required. Thus, for any particular patient, the VRP is programmed to extend just beyond the measured intrinsic conduction time. A pacemaker in accord with this invention typically allows programming of VRP through a range, e.g., from 150 to 500 ms, in steps of 10 ms.

However, since IVCD rarely is greater than 280 ms, VRP would generally be programmed through a range from about 150 to 300 ms in the practice of this invention. The LOC detection algorithm recognizes LOC after a pattern of VRs, e.g., one or more VRs, but does not react to VSs, which occur outside the VRP window.

Figure 3:
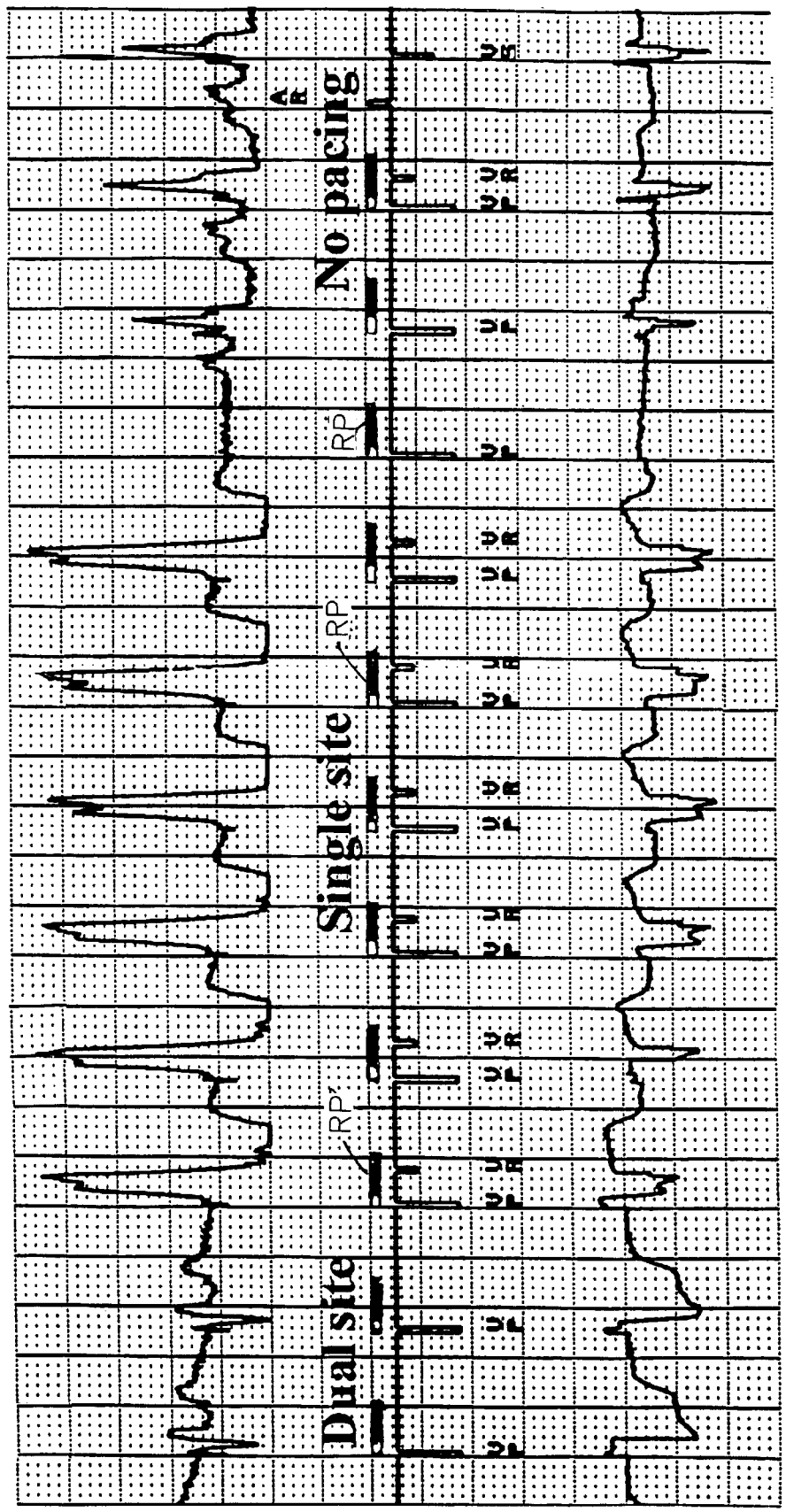
FIG. 3 is a series of curves illustrating the effect of decreasing the energy (PO) in dual site pulses, and illustrating VPs which represent simultaneous pacing events and the detection of VRs when capture has been lost at a single site.

Referring now to FIG. 3, there is shown a series of curves illustrating delivery of progressively lower PO pacing pulses to each ventricle, resulting in (DSC) dual site capture (dual ventricular capture), then (SSC) single site capture (single ventricular capture), and finally complete (LOC) loss of capture (capture in neither ventricle). The upper curve shows a surface ECG, corresponding to continued decrease in PO of the dual pulses occurring simultaneously as pulse pairs. The marker channel indicates delivery of dual pulses, indicated as VP; it indicates sensed signals during the refractory interval, indicated as VR; and it shows the blanking period, typically 8–16 ms following the VP, followed by the refractory interval, indicated as RP. The bottom curve represents the intracardiac signal as obtained by the pacemaker. The patient represented by FIG. 3 has a LBBB, as well as an Intra-Atrial Conduction Defect (IACD), resulting in slow P wave propagation from RA to LA. The first two pulse pairs had sufficient PO to obtain dual site capture. Thus, for these two cycles, the QRS and T wave portions can be seen following the delivery of the VP. However, upon delivery of the third pair of pulses, one ventricle, in this case left ventricle, is not captured. The surface ECG shows an extended signal manifested as an increase in QRS duration, the effect of LBBB, which also can be seen in the bottom curve (EGM signal). As shown on the marker channel, a VR is obtained. After six consecutive single site captures, the PO is reduced to the point where there is no capture in either ventricle. As can be seen, after the first cycle of no capture, no signal is sensed.

After the second no capture pulse pair, an intrinsic signal is seen, which apparently is blanked. After the third such no capture pulse pair, the intrinsic signal is sensed within the RP, as indicated by the VR on the marker channel, confirming LOC.

Examination of FIG. 3 indicates that it is extremely unlikely that the pacemaker would have a no pacing cycle, where neither chamber was captured.

Fluctuations of acute and chronic thresholds at each site are independent of each other, such that the thresholds of the two sites will never be exactly the same. A change in either threshold with time would initially result in one ventricle or the other (or one atrium or the other) experiencing LOC, which would result in a VR and automatic increase in PO. The invention capitalizes on the observation that when capture is lost at one of the dual pacing sites, the conduction delay results in an intrinsic signal detection after blanking but before the end of the refractory period enabling an automatic increase of the pacing stimulus PO, e.g., increase of either amplitude or width, to regain capture at both sites. Of course, in a normal heart the intrinsic conduction delay from RV to LV would be +50–60 ms, and would be within the absolute blanking period, but bi-ventricular pacing would not be indicated for such a patient.

Figures 4A, 4B:
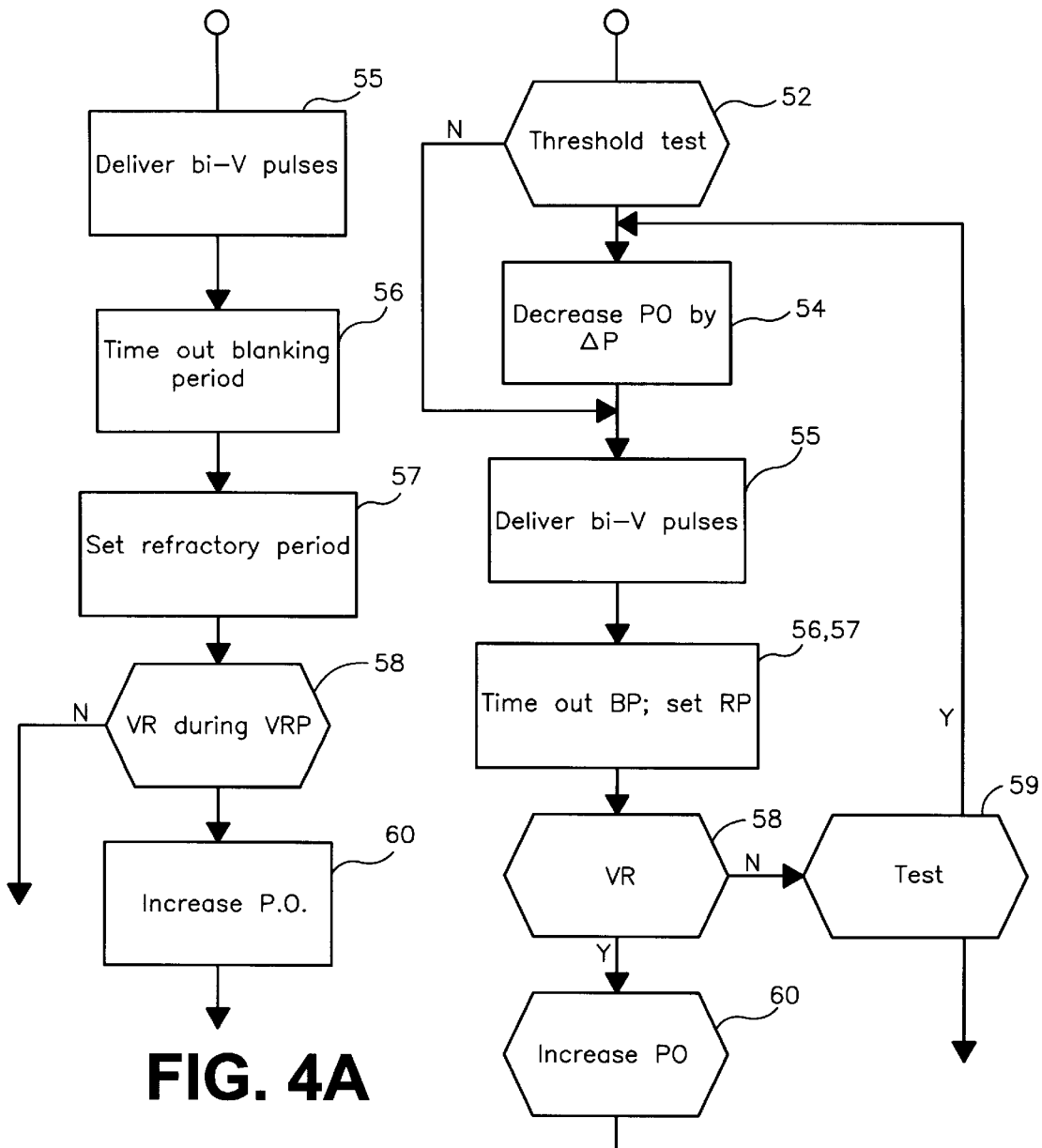
FIG. 4A is a simplified flow diagram showing the primary steps taken by a pacemaker in accordance with this invention for continuously monitoring for loss of capture and automatically increasing pulse output in the event of single site loss of capture.
FIG. 4B is a flow diagram which includes initiation of a threshold test.

Referring now to FIG. 4A, there is shown a flow diagram of the basic steps of monitoring capture or no capture. At 55, the pacemaker delivers the bi-ventricular pace pulses, followed by the timing out of a blanking period at 56. Following this, the pacemaker times out the refractory period (VRP), as indicated at block 57, and at 58 waits to see if there is a VR, i.e., a sense of an intrinsic signal during the VRP. If not, dual capture is presumed, and the routine exits and awaits the next cycle. If yes, at 60 the pacemaker automatically increments the PO, in order to maintain PO safely above threshold. The amount of increase is a design variable, and can be programmed accordingly. Alternatively, the routine may require detection of X consecutive VRs before implementing an increase in PO, e.g., 2–5 VRs; or other patterns of detected VRs.

Referring to FIG. 4B, there is shown a variation of FIG. 4A, wherein the pacemaker can conduct a threshold test. A test may be automatically initiated, e.g., every N days, or may be initiated by external programming. If the test is called for, as indicated at 52, then at 54 the pacemaker automatically decreases the PO by ΔP. Following this, steps 55–58 are carried out. At 58, if no VR is sensed, this means that there is still dual site capture, and the routine branches to block 59 to determine whether a test is in progress. If yes, the routine returns to 54, and again decreases the PO; if no, the routine exits. This continues until a VR is found, and following this PO is increased as indicated at block 60.

It is to be understood that the flow diagrams 4A, 4B apply equally to a pacemaker with a single sensing channel, or a pacemaker with separate sensing channels. Thus, for a pacemaker with a single sensing channel, if a VR is sensed, then the increase of PO applies to each pulse of the dual site pulse pair. If dual sensing channels are utilized, the increase of PO applies only to the pulses outputted to the heart chamber where failure of capture had been indicated by the VR.

It is thus seen that there is a very simple yet elegant procedure provided for reliably sensing loss of capture in dual site pacing, for patients where the conduction dysfunction causes either an interventricular delay or interatrial delay in excess of the blanking period.

What is claimed is:

1. A cardiac pacing system with bi-ventricular pacing of a patient, comprising:

pulse means for generating a pair of concurrent pacing pulses, lead means for delivering one of said concurrent pacing pulses to the patient's right ventricle and one of said concurrent pacing pulses to the patient's left ventricle, said lead means further having electrode means for sensing excitation sinals in each of said ventricles;

refractory means for timing out a refractory interval following each delivery of a said pair of concurrent pacing pulses, and sensing means electrically connected to said lead means for determining when a said excitation signal has been sensed in at least one ventricle by said electrode means during a said refractory interval; and LOC means for indicating loss of capture in at least one of said ventricles in response to sensing one or at least ventricular excitation signal during said refractory interval; further comprising pulse output control means for increasing the power output of at least one pulse of said pulse pair in response to an indicated loss of capture;

wherein said pulse means delivers two pulses of equal power output at substantially the same time, and said control means increases the power output of each said pulse of said pair to the same level.

2. The system as described in claim 1, wherein said control means controls said pulse mean is to deliver said pair of pulses in a timed relation so that a first of said pulses is delivered a predetermined short time interval before the second of said pulses, and said refractory means times out said refractory interval following the time of delivery of said first pulse.

3. The system as described in claim 1, wherein said lead means comprises a left lead having left distal electrode means for sensing signals in the patient's left ventricle, and a right lead having right distal electrode means for sensing signals in the patient's light ventricle.

4. The system as described in claim 1, wherein said sensing means comprises dual sensing channels, a first of said channels being electrically connected to said lead means to receive sensed signals from the patient's left ventricle, and the second of said channels being electrically connected to receive signals from the patient's right ventricle.

5. The system as described in claim 4, wherein said LOC means provides an indication of either ventricle in which an excitation was sensed, and comprising control means for increasing the power output of the pulse for delivery to either said indicated ventricle.

6. The system as described in claim 1, comprising blanking means for timing out a blanking interval following each delivery of a said pair of pulses, and wherein said refractory means comprises means for initiating said refractory interval at the end of said blanking interval.

7. The system as described in claim 6, said control means having threshold test means for decreasing said power output until loss of capture is indicated in at least one of said ventricles.

8. A dual site cardiac pacing system, providing fore delivery of substantially concurrent pacing pulses to dual sites in a patient's heart, said system having a pacemaker and leads connected to said pacemaker for delivering pacing pulses to said sites and for obtaining cardiac senses from each of said sites, said pacemaker comprising:

pulse generator means for cyclically generating said concurrent pulses;

control means for controlling the timing and power output of said concurrent pulses;

refractory means for timing out a programmable refractory interval following each generation of said concurrent pulses;

sensing means for sensing when at least one said cardiac sense occurs at one of said sites during a said refractory interval; and LOC means for indicating loss of capture at at least one of said sites when at least one said cardiac sense is sensed during said refractory interval;

comprising first lead means for delivery of pacing pulses to the patient's left ventricle and for obtaining left ventricular senses, and a second lead means for delivery of pacing pulses to the patient's right ventricle and for obtaining right ventricular senses; wherein said control means comprises response means for responding to an indicated less of capture by increasing the output level of at least one of said concurrent pulses in response thereto; wherein said control means has means for increasing the output level of the pulses delivered to both of said dual sites.

9. The pacing system as described in claim 8, wherein said sensing means comprises first means for sensing when, a ventricular sense occurs in the left ventricle during said refractory interval, and second means for sensing when a ventricular sense occurs in the right ventricle during said refractory interval, and said LOC means comprises VR means for indicating the ventricle in which a ventricular sense has occurred during the refractory interval (VR).

10. The pacing system as described in claim 9, wherein said response means comprises means for increasing the output level of the pulses delivered to the ventricle where a VR has been indicated.

11. The pacing system as described in claim 8, wherein said sensing means comprises means for determining a pattern of cardiac senses during the refractory interval, and said LOC means indicates loss of capture when a said pattern is determined.

12. The pacing system as described in claim 8, comprising programming means for programming said refractory interval to a value in the range of about 150–300 ms.

13. A dual site cardiac pacing system, providing for delivery of substantially concurrent pacing pulses to dual sites in a patient's heart, said patiernt's heart being characterized by an Intraventricular Conduction Delay of up to 300 ms, said system having a pacemaker and leads connected to said pacemaker for delivering pacing pulses to said sites and for obtaining cardiac senses from cach of said sites, said pacemaker comprising:

pulse generator means for cyclically generating said concurrent pulses;

control means for controlling the timing and power output of said concurrent pulses;

refractory means for timing out a programmable refractory interval as set to a value greater than said patient TVCD following each generation of said concurrent pulses;

sensing means for sensing when at least one said cardiac sense occurs at one of said sites during a said refractory interval;

LOC means for indicating loss of capture at at least one of said sites when at least one said cardiac sense is sensed during said refractory interval; and response means for responding to an indicated loss of capture by increasing the output level of at least one of said concurrent pulses in response to an indicated LOC.

* * * * *

UNITED STATES PATENT AND TRADEMARK OFFICE
CERTIFICATE OF CORRECTION

PATENT NO.     : 6,148,234
DATED          : November 14, 2000
INVENTOR(S)    : Struble It is certified that error appears in the above-identified patent and that said Letters Patent is hereby corrected as shown below:

Column 7,
Line 33, change "patient's light ventricle" to -- patient's right ventricle --.

Column 8,
Line 54, change "TVCD following" to -- IVCD following --.
Line 19, change "when a" to -- when a --.

Signed and Sealed this

Eighteenth Day of March, 2003

JAMES E. ROGAN
*Director of the United States Patent and Trademark Office*